United States Patent [19]
Vojdani

[11] Patent Number: 5,707,816
[45] Date of Patent: Jan. 13, 1998

[54] IMMUNOLOGICAL CROSS REACTIVITY BETWEEN CANDIDA AND HUMAN TISSUE OR FOOD ANTIGENS

[75] Inventor: Aristo Vojdani, Los Angeles, Calif.

[73] Assignee: Immunosciences Lab, Inc.

[21] Appl. No.: 796,411

[22] Filed: Feb. 6, 1997

[51] Int. Cl.$^6$ .................. G01N 33/53; G01N 33/567; G01N 33/554; G01N 33/542

[52] U.S. Cl. .................. 435/7.21; 435/7.31; 435/7.32; 435/7.9; 435/7.92; 435/7.93; 435/7.94; 435/7.95; 436/174; 436/514; 436/530

[58] Field of Search .................. 435/7.21, 7.31, 435/7.32, 7.9, 7.92, 7.93, 7.94, 7.95; 436/174, 514, 530

[56] References Cited

PUBLICATIONS

Jawertz et al. (Medical Microbiology 19th ed. pp. 323–324), (1991).
Monteagudo et al. (Amer. J. Clin. Path. vol. 103 pp. 130–135) (Feb. 1995).
Green et al. (Biochemical Journal 211(2) pp. 481–493) May 1, 1983.
G. Edge, et al., (1980), "Antibodies in different immunoglobulin classes to *Candida albicans* in allergic respiratory disease", *Clinical Allergy* 10:47–58.
E.A. El–Maghrabi, et al., (1990), "Characterization of *Candida albicans* epidermolytic proteases and their role in yeast–cell adherence to keratinoctes", *Clinical and Experimental Dermatology* 15:183–191.
R.S. Fujinami, et al., (1983), "Molecular mimicry in virus infection: Crossreaction of measles virus phosphoprotein or of herpes simplex virus protein with human intermediate filaments".*Proc. Natl. Acad. Sci. USA* 80:2346–2350.
J. Gutierrez, et al., (1993), "Circulating Candida Antigens and Antibodies: Useful Markers of Candidemia", *Journal of Clinical Microbiology* 31(9):2550–2552.
V. Hopwood, et al., (1985) "A Comparison of Methods for the Detection of *Candida* Antigens. Evaluation of a New Latex Reagent", *Journal of Immunological Methods* 80;199–210.

S.R. Kain, et al., (1994), "Human Multiple Tissue Western Blots: A New Immunological Tool for the Analysis of Tissue–Specific Protein Expression", *BioTechniques* 17(50): 982–987.
T. Lehner, (1970), "Serum Flourescent Antibody and Immunoglobulin Estimations in Candidosis ", *J. Med. Microbiol.* 3:475–481.
S. Mathur, et al., (1977) "*Humoral Immunity in Vaginal Candidiasis*", *Infection and Immunity* 15(1):287–294.
S. Mathur, et al., (1980), "Anti–Ovarian and Anti–Lymphocyte Antibodies in Patients with Chronic Vaginal Candidiasis", *Journal of Reproductive Immunology* 2:247–262.
M.B.A. Oldstone, (1989), "Virus–induced Autoimmunity: Molecular Mimicry as a Route to Autoimmune Disease", *Journal of Autoimmunity* 2(Supplement):187–194.
M.F. Price, et al., (1977), "Phospholipase Activity in *Candida albicans*", *Sabouraudia* 15:179–185.
P. Saegner, et al., "(1982), Progresive Ardenal Failure in Polyglandular Autoimmune Disease", *Journal of Clinical Endocrinology and Metabolism* 54(4):863–868.
J. Savolainen, et al., (1990), "Immunoblotting analysis of concanaval in A–isolated allergens of *Candida albicans*" *Allergy* 45:40–46.
Y. Shoenfeld, et al., (1988), "Mycobacteria and autoimmunity", *Immunology Today* 9(6):178–182.
J. Srinivasappa, et al., (1986), "Molecular Mimicry: Frequency of Reactivity of Monoclonal Antiviral Antibodies with Normal Tissues", *Journal of Virology* 57(1) :397–401.
N. Tala, et al., (1990), "A Conserved Idiotype and Antibodies to Retroviral Proteins in Systemic Lupus Erythematosus", *J. Clin, Invest.* 85:1866–1871.

*Primary Examiner*—Anthony C. Caputa
*Assistant Examiner*—Mark Navarro
*Attorney, Agent, or Firm*—Knobbe, Martens, Olson & Bear, LLP

[57] ABSTRACT

A method of determining immunological cross reactivity between Candida and human tissue or food antigens. Tissue antigen preparations or food extracts are analyzed by electrophoresis. Cross reacting antigens are identified by immunoblotting using anti-Candida antisera.

14 Claims, No Drawings

IMMUNOLOGICAL CROSS REACTIVITY BETWEEN CANDIDA AND HUMAN TISSUE OR FOOD ANTIGENS

FIELD OF THE INVENTION

The present invention relates to the detection of antibodies to Candida which cross react with mammalian tissue antigens and food antigens. The invention also relates to the identification of these cross reactive antigens.

BACKGROUND OF THE INVENTION

Autoimmunity is the result of multiple factors, including immune defects, hormonal constellation, genetic predisposition and environmental factors (Schoefeld et al., *Immunol. Today*, 9:178–181, 1988). The most important of these factors are infectious agents such as viruses, bacteria and parasites. Antigenic similarity or molecular mimicry between antigens of infectious agents and host tissues is believed to play a significant role in the induction of autoimmune disease by microorgasms (Fujinami et al., *Proc. Natl. Acad Sci. U.S.A.*, 80:2346–2350, 1983). Antigenic cross-reactivity between host and bacteria is exemplified by blood group substances and bacterial polysaccharides; cardiac tissue and streptococcal proteins; and kidney tissue and *E. coli* polysaccharides. Viruses may also induce autoimmune responses through shared determinants on molecules notably present on host cells, by altering the host immune system, or by causing the expression or release of "normally sequestered" self antigens.

Autoantibodies are frequently found in the sera of virus-infected individuals, both during and after infection. For example, after infection with Epstein-Barr virus (EBV), antibodies reacting with intermediate filaments of cells, immunoglobulin or thyroglobulin were detected (Oldstone, *J. Autoimmunity*, 2(Suppl.):187–194, 1989; Srinivasappa et al., *J. Virology*, 57:397–401, 1986; Talal et al., *J Clin. Invest.*, 85:1886–1871).

Candida is a heterogeneous genus of yeast. At least six Candida species have been implicated as human pathogens, although the majority of Candida infections are caused by *Candida albicans* and *Candida tropicalis*. Candida is most often found in the mouth, feces and vagina and results in substantial morbidity and mortality in immunosuppressed patients or in those patients superinfected with the fungus. By virtue of widespread mucosal contact with this organism, antibody formation against it is common and begins early in life. Candida antibodies have been shown to belong to the IgA, IgG, IgM and IgE immunoglobulin classes (Edge et al., *Clin. Allergy*, 10:47–58, 1980). The predominant antibody in patients with systemic infectious candidiasis is Candida IgG (Lehner, *J. Med. Microbiol*, 3:475–481, 1970), whereas in patients with recurring vaginal candidiasis, the antibody response is primarily local and consists mainly of secretory IgA (Mathur et al., *Infect. Immun.*, 15:287–294, 1977). Circulating levels of Candida antigens, antibodies and immune complexes have been used for the diagnosis of candidemia (Gutierrez et al., *J. Clin. Microbiol.*, 1:2550–2552, 1993). *Candida albicans* has been reported to be a pathogenic factor in selected cases of urticaria, asthma, irritable bowel disease and psoriasis. Candida has been implicated in polyglandular autoimmune disease in which high titers of organ-specific antibodies to endocrine organs and parietal cells of the stomach were discovered (Saenger et al., *J. Clin. Endo. Metabol.*, 54:863–868, 1982). Mathur et al. (*J. Reprod. Immunol*, 2:247–262, 1980) found that patients with chronic vaginal candidiasis (CVC) had one or more cross-reactive antigens on ovarian follicles, $T_h$ cells and Candida since absorption of patient sera with Candida cells, ovarian follicle cells or thymocytes reduced all three antibody titers. Despite this indirect association between CVC and autoantibodies, immunological cross reactivity between Candida antigens and human antigens was not shown.

Individuals with Candida infection often develop multiple food intolerances, making it difficult for them to maintain a normal lifestyle. There is general agreement that a low carbohydrate diet is mandatory, although most patients do well on a diet avoiding refined sugars and large amounts of honey, maple syrup and fruit juices. Milk should also be restricted due to its high lactose content. Elimination of yeast-containing foods is also recommended due to the high degree of apparent cross-sensitization between *Candida albicans* and brewer's/baker's yeast. However, not all patients sensitive to *Candida albicans* will be sensitive to yeast containing foods and ingestion of a yeast-containing food does not in itself augment *Candida albicans* growth.

Thus, it is desirable to identify whether a particular mammalian tissue or food contains antigens which cross-react with Candida antigens since antibody production against such antigens may cause development of an autoimmune disease. The present invention provides such a method.

SUMMARY OF THE INVENTION

One embodiment of the present invention is a method of detecting immunological cross reactivity between a plurality of tissue antigens and Candida antigens in an individual infected with Candida, comprising the steps of:

isolating antisera from the individual;

contacting the tissue antigens with the antisera; and determining whether the antisera binds one or more of the tissue antigens.

Preferably, the contacting and determining steps comprise enzyme linked immunosorbent assay or immunodiffusion; more preferably, they comprise separating the tissue antigens by gel electrophoresis and transferring the antigens to a membrane prior to the contacting step. Advantageously, one or more of the tissue antigens has a molecular weight of about 36 kDa or 72 kDa.

Another embodiment of the invention is a method of detecting immunological cross reactivity between a food antigens and Candida antigens in an individual infected with Candida, comprising the steps of:

isolating antisera from the individual;

contacting the food antigens with the antisera; and determining whether the antisera bind one or more of the food antigens.

Preferably, the contacting and determining steps comprise enzyme linked immunosorbent assay or immunodiffusion; more preferably, they comprise separating the tissue antigens by gel electrophoresis and transferring said antigens to a membrane prior to the contacting step. According to one aspect of this preferred embodiment, the food antigens have molecular weights between 1 kDa and 250 kDa. Advantageously, they have molecular weights between about 10 kDa and about 90 kDa.

Another embodiment of the invention is a method of determining a diet plan for a patient having a Candida infection, comprising:

isolating serum from the patient;

contacting a plurality of food antigens with the antisera; and determining whether the serum binds one or more of said food antigens, wherein said food antigens which bind said serum are avoided.

Preferably, the contacting and determining steps comprise enzyme linked immunosorbent assay or immunodiffusion; more preferably, they comprise separating the tissue antigens by gel electrophoresis and transferring the antigens to a membrane prior to the contacting step. In one aspect of this preferred embodiment, the food antigens have molecular weights between 1 kDa and 250 kDa. Preferably, the food antigens have molecular weights between about 10 kDa and about 90 kDa.

DETAILED DESCRIPTION OF THE PREFERRED EMBODIMENTS

The present invention provides a method for identifying cross-reactivity between Candida antigens and either food or tissue antigens. Although the studies described below involve detection of cross reactivity between *C albicans* and food or tissue antigens, the detection of cross reactive antigens from other Candida species, particularly *C. tropicalis*, is also within the scope of the invention. Candida-positive human sera were screened based on whether they were seronegative or seropositive for autoimmune (thyroid, ovary and adrenal) antibodies. Compared to tissue antibody-negative sera and healthy control sera, samples from positive tissue antibody subjects exhibited significantly higher levels of Candida IgG (P<0.001), IgM (P<0.001) and IgA (P<0.01). While Candida antibodies were elevated in 60% of tissue antibody positive samples, these antibodies were present in only 7.5% of tissue antibody negative subjects and in 10% of healthy controls. These positive antibodies and rabbit anti-Candida antibodies were simultaneously analyzed by double radial immunodiffusion and Western blotting against Candida and tissue antigens, illustrating distinct cross-reactivity between Candida and tissue antigens. Western blotting indicated that the common antigens were in the 72 kDa and 36 kDa. Absorption of sera containing high levels of Candida antibodies with tissue antigens caused a 10–15% reduction in antibody titers. Moreover, treatment of thyroid antibody positive sera resulted in a similar reduction in thyroid antibody levels. These reductions in antibody levels demonstrate cross-reactivity between Candida antigens and mammalian tissue antigens. This cross-reactivity may be associated with the pathogenic role of Candida in the development of autoimmune diseases.

Cross reactivity was also observed between Candida and various food antigens. Candida and various food antigens were analyzed by sodium dodecyl sulfate-polyacrylamide gel electrophoresis (SDS-PAGE) and Western blotting using human anti-Candida antiserum. Numerous protein bands were detected by the anti-Candida antiserum. Absorption of sera containing high levels of Candida antibodies with food and tissue antigens caused a 10–40% reduction in antibody titers as determined by the reduction in optical density in an enzyme-linked immunosorbent assay (ELISA), further confirming the cross reactivity observed in Western blotting experiments.

In a preferred embodiment, Western blotting is used to detect immunological cross reactivity between Candida and food or tissue antigens. However, the use of any suitable assay for detection of such cross reactivity is within the scope of the invention. Such well known assays include, for example, ELISA, agglutination, double radial immunodiffusion (Ouchterlony assay), fluorescent antibody labeling and radioimmunoassay. Candida antigens comprise proteins, glycoproteins, glycolipids, peptides and other epitopes having molecular weights between about 1 kDa and 250 kDa. Dietary antigens which cross react with Candida antigens comprise similar molecules, more specifically molecules with molecular weights of between about 10 kDa and about 90 kDa. The antigens found in Candida and foods which cross react with mammalian tissues may include, for example, enzymes such as proteases (El-Maghrabi et al., *Clin. Exp. Dermatol.*, 15:183–191, 1990), phospholipases Price et al., *Sabouraudia*, 15:179–185, 1977) and alcohol dehydrogenase (Shen et al., *Clin. Exp. Allergy*, 21:675–681, 1991).

The method of the present invention is used to determine whether an individual having a Candida infection has antibodies which cross react with tissue antigens. The patient's sera is also tested against a panel of food antigens to determine which foods cross react with Candida antibodies. The cross-reacting foods can be avoided, thus preventing many allergic reactions.

The following examples provide illustrative methods for carrying out preferred steps in conjunction with the practice of the present invention. As such, these examples are provided for illustration purposes only and are not intended to limit the invention.

EXAMPLE 1

Human Antisera

Sera were chosen from 100 patients diagnosed with autoimmune disease screened by a clinical laboratory. The autoimmune disease was noted by the examining physician based on medical history and physical examination. Sera were classified based on negative or positive titers for thyroid, adrenal, ovary and parietal cell antibodies. Healthy control sera were obtained from laboratory employees having no history of autoimmune disease. All sera were negative for HIV, Treponema pallidum, and Hepatitis B.

*C. albicans* antigens were prepared as described below.

EXAMPLE 2

Preparation of *C. albicans* Antigens

*C. albicans* was isolated from a clinical specimen and identified according to the taxonomic criteria of Lodder (*The Yeasts*, North-Holland Publishers, London, pp.215) as serotype A. Yeast was grown in Sabouraud medium containing polypeptone yeast extract and glucose. The culture was incubated at 28° C. with slight agitation until mid-logarithmic phase, harvested by centrifugation and washed three times with 0.1M phosphate buffered saline (PBS). Cytoplasmic and mannan antigens were prepared using a modified method of Hopwood (*J. Immunol. Meth.*, 80:199–210, 1985) and Savolainen et at. (*Allergy*, 45:40–46, 1990). Cells were disrupted by homogenization and centrifuged at 15,000×g for 20 minutes. The supernatant containing cytoplasmic proteins was analyzed for enolase content which was 63%, with 37% being other cytoplasmic antigens. The mannan/mannoprotein concentration after affinity purification was 6 mg/ml.

Candida-specific immunoglobulin levels were measured as described in the following example.

EXAMPLE 3

Measurement of Candida-specific Antibodies

Candida-specific IgG, IgM, and IgA were measured by ELISA. Microtiter wells were coated overnight at 4° C. with 5 μg Candida cytoplasmic proteins diluted in 50 mM carbonate buffer, pH 9.6. This optimum coating concentration was determined be checkerboard titration of antigens against positive and negative human sera. Sensitized plates were washed three times in PBS containing 0.05% Tween-20 (PBST). Two hundred μl of each serum diluted from 1:200 were added to three sets of duplicate wells and incubated for 12 hours at 4° C. After washing as described above, an aliquot (200 μl) of mouse monoclonal anti-human IgG, IgM or IgA was added to a set of duplicate wells. The plate was incubated for 12 hours at 4° C., washed as before and 200 μl horseradish peroxidase (HRP)-labeled goat anti-mouse IgG was added. Antibodies labeled with phosphatase, urease and other enzymes are also within the scope of the invention. After the third incubation and final washing, freshly prepared HRP substrate (0.4 mg/ml o-phenylenediamine dihydrochloride, Sigma) and 6% (v/v) $H_2O_2$ were added (100 μl/well). The reaction was stopped 30 minutes later by addition of 4 N $H_2SO_4$ (25 μl/well) and the optical density of each well at 492 nm was determined using an automated microplate reader (Dynatech Laboratories, Va.). Results were expressed as arbitrary ELISA units. This value was defined as the last dilution of serum giving an optical density twice that of the negative control.

Sera from 100 different patients were examined for thyroid, ovary, adrenal and Candida antibody levels and were classified in four different groups as shown in Table 1. Sera were considered positive for tissue antibodies only if levels higher than three standard deviations of negative controls were present. All positive or negative samples for tissue antibodies, as well as sera from 20 healthy controls, were measured simultaneously for Candida IgG, IgM and IgA antibodies. The results (Table 1) indicate an overall elevation of Candida antibodies in the positive thyroid, ovary and adrenal antibody specimens compared to the tissue antibody negative sera. 60% of the tissue positive sera contained Candida antibodies, while only 7.5% of tissue negative sera and 10% of control sera contained Candida antibodies. The P values were <0.001, <0.001 and <0.01 for IgG, IgM and IgA, respectively. By comparing tissue positive to tissue negative antibodies, Candida antibody values were determined to be highly significant for IgG and IgM (P<0.001) and less significant for IgA antibodies (P<0.01). Sera with highly positive (>10,000) and negative (<3,000) were chosen for further analysis.

TABLE 1

|  | IgG | IgM | IgA |
|---|---|---|---|
| Healthy control (n = 20) | 2683 ± 1274 | 1325 ± 582 | 2476 ± 1832 |
| Negative tissue antibodies (n = 40) | 2940 ± 1420 | 1250 ± 635 | 2690 ± 1623 |
| Positive thyroid antibodies (n = 20) | 5220 ± 2416 | 4680 ± 3782 | 3700 ± 1481 |
| Positive ovarian antibodies (n = 20) | 4885 ± 2170 | 3960 ± 3219 | 4100 ± 2112 |
| Positive adrenal antibodies (n = 20) | 6187 ± 1969 | 5187 ± 2423 | 3920 ± 161 |

EXAMPLE 4

Preparation of Rabbit anti-Candida Antibodies

Cytoplasmic *C. albicans* antigens prepared in accordance with Example 2 (5 mg) were emulsified in complete Freund's adjuvant (CFA) and intramuscularly injected every other week into three rabbits. The fourth rabbit was injected with CFA alone and used as a control serum. *S. aureus* lysate antigen in CFA was also used as a control. After seven injections, the animals were bled and immunoglobulin levels were determined using the ELISA described in Example 3.

Mammalian tissue homogenates were prepared as described in the following example.

EXAMPLE 5

Preparation of Tissue Homogenates

Human placental and mucosal acetone protein powder and myelin basic protein were obtained from Sigma. Tissue from the capsule surrounding the silicone breast implant of three different women with post-surgical complications were obtained from AMDL (City of Industry, Calif.). Histopathological examination of this tissue indicated the presence of striated muscle, maturing collagen, elastin, reticulin, lymphocytes, plasmacytes and macrophages. Ovary, adrenal gland, thyroid, thymus, liver, pancreas, spleen, brain and kidney were obtained from either animal tissues (Pel-Freez biologicals, Rogers, AR, or from a normal caucasian female, age 21, who died of a gunshot wound eight hours prior to obtaining tissue. Tissues were stored at −80° C. prior to use.

Human and animal tissues were thawed by gently swirling in ice-cold homogenization buffer containing 0.1M Tris-HCl, pH 7.5, 15% (v/v) glycerol, 0.2 mM EDTA, 1.0 mM dithiothreitol, 10 μg/ml leupeptin and 1.0 mM phenylmethylsulfonylfluoride (PMSF) (all from Sigma). Several changes of buffer were used to remove blood from the tissues and to equilibrate to 4° C. After removal of fat and connective tissue, the samples were homogenized in two volumes of cold homogenization buffer using a Polytron homogenizer. Homogenization was performed within 5–10 minutes after thawing the tissue. For heart and skeletal muscle samples, the pH was monitored and adjusted to 7.5 using 0.01 N NaOH. The tissue homogenate was transferred to a chilled glass dounce homogenizer (Wheaton, Millville, N.J.) (clearance 0.07 mm) and further homogenized with 50 strokes on ice. The tissue homogenate was treated with a nuclease solution containing 50 mM Tris-HCl, pH 7.0, 0.1 mg/ml DNase I (Sigma), 5 mM $MgCl_2$ for 20 min on ice. After centrifugation at 15,000×g, the final tissue homogenate was aliquoted, frozen on dry ice/ethanol and stored at −80° C. (Kain et al., *Biotechniques*, 17:982–987, 1994). Protein concentrations were determined using the Bradford method with bovine serum albumin as the standard. Food antigens were purchased from Iatric Corp., Tempe, Ariz. Similar antigens are also available from other companies specializing in the preparation of allergens for allergy testing.

Antigenic cross reactivity between anti-Candida sera and mammalian tissue antigens was initially confirmed by formation of precipitation lines as described below.

EXAMPLE 6

Double Radial Immunodiffusion

As a preliminary test for cross-reactivity, immunodiffusion was performed using rabbit anti-Candida (300 μl) in the center well and Candida and tissue antigens (200 μg each in 100 μl buffer) in the outer wells. After a 24 hour incubation, five precipitation lines were observed with Candida antigen and one or two lines with each of the tissue antigens. Similar results were obtained using human serum having high titers of anti-Candida and tissue antibodies. No precipitation lines were present if low titers of Candida or Tissue antibodies were used. Neither pre-immune rabbit serum nor rabbit anti-*S. aureus* antigens reacted with the Candida and tissue antigens.

To determine which antigens were cross reactive between Candida and tissue or food, Western blotting was performed as described below.

EXAMPLE 7

Western Blotting of Food and Tissue Antigens

Tissue homogenates, food antigens and Candida antigens were solubilized by heating at 90° C. for 5 minutes in sample buffer containing 62.5 mM Tris-HCl, pH 6.8, 2% (w/v) SDS, 10% (v/v) glycerol, 0.1% bromophenol blue and 80 mM dithiothreitol. SDS-PAGE was performed according to Laemmli (Laemmli, *nature*, 227:680–685, 1970) using either a 10% or 12% resolving gel to separate the tissue antigens and food antigens. Each sample contained 100 µg total protein isolated from Candida, 20 µg tissue or 20 µg food antigens. Gels were stained with Coomassie blue to visualize proteins present in the samples.

Electrophoretic transfer of proteins from the SDS gel to nitrocellulose membranes was performed using a semi-dry blotting apparatus in cold buffer containing 25 mM Tris-HCl, pH 8.3, 192 mM glycine, 20% (v/v) methanol and 0.1% (w/v) SDS (Sigma) according to the manufacturer's instructions. The membrane was rinsed twice in PBS, then incubated for 1 hour at room temperature in blocking buffer (PBS containing 1% w/v nonfat dry milk and 0.1% v/v Tween-20). Membranes were incubated in the same buffer, with the addition of 0.5% bovine serum albumin (BSA) and primary antibody. The primary antibody, either rabbit anti-Candida or human serum having highly positive or negative ELISA values from Example 3, was diluted 1:200 in blocking buffer prior to addition to the incubation solution. The membranes were washed with blocking buffer, then incubated for 1 hour at room temperature in an alkaline phosphatase-conjugated secondary antiserum diluted in blocking buffer. The membranes were washed, followed by addition of color development reagents (Bio-Rad, Richmond, Calif.). For the food antigen blot, the ECL Western blot development protocol was used (Amersham, Arlington Heights, Ill.) according to the manufacturer's instructions.

SDS-PAGE analysis of Candida and different tissue antigens using 10% gels or a combination of 7% and 12% gels showed several bands in tissue antigen preparations at positions similar to Candida antigens. Rabbit or calf tissue homogenate was significantly similar to human tissue. A 72 kDa band was common to all tissues and to Candida.

In Western blotting, rabbit anti-Candida reacted with this 72 kDa band as well as several additional bands in capsule, placenta, ovary, adrenal, spleen, thyroid and brain. Anti-Candida sera from the second rabbit reacted similarly to that from the first rabbit. Sera from rabbits immunized with *S. aureus* antigens in CFA did not react with Candida and tissue antigens. Two different sera from patients with high levels of Candida and tissue antibodies reacted with Candida, and different tissues showed different reactivity. Although many bands were detected with Candida and different tissues, the common reactivity was located at about 72 kDa in all tissues and in some tissues at about 36 kDa. Both sera showed similar reactivities. Sera from patients with low levels of Candida and tissue antibodies (control sera, negative Candida and tissue antibody sera) did not react with Candida antigens.

Many food antigens also cross reacted with Candida antigens, including potato, halibut, brewer's yeast, baker's yeast, mango, brussel sprouts, tangerine, chili pepper, apple, celery and lamb. The 72 kDa antigen was also present in many foods, as were antigens having molecular weights of about 90, 75, 70, 68, 67, 65, 55, 48, 46, 44, 43, 40, 36, 30, 25, 15 and 10 kDa.

To further confirm antigenic cross reactivity between anti-Candida sera and food or tissue antigens, absorption studies were performed as described in the following example.

EXAMPLE 8

Absorption of Rabbit and Human Anti-Candida Sera

Rabbit anti-Candida or human anti-Candida sera with elevated Candida IgG or IgM levels were absorbed with Candida, tissue antigens or food antigens. To one ml of serum from rabbits immunized with *C. albicans* or patients with elevated Candida antibodies, 0.1 ml of PBS, 0.1 ml of food extracts or 0.1 ml (500 µg) of tissue antigens was added. Samples were incubated for 2 hours at 37° C., then overnight at 4° C. Samples were centrifuged at 4,000×g and supernatants were removed for measurement of Candida antibody levels by ELISA to determine how much antibody was absorbed by the Candida, tissue or food antigens. Optical densities were compared to the sera from before absorption. The results for tissue antigen absorption are shown in Table 2 and in both rabbit and human sera, Candida antibodies were almost completely removed by incubation with Candida. When sera were incubated with thyroid or adrenal extracts, a 10–15% reduction in optical densities was observed due to absorption of Candida antibodies with these antigens. These antibodies were not present in the serum of the control rabbit injected with CFA alone.

TABLE 2

| | Before absorption | | Absorption with Candida | | Absorption with thyroid extract | | Absorption with adrenal extract | |
|---|---|---|---|---|---|---|---|---|
| | IgG | IgM | IgG | IgM | IgG | IgM | IgG | IgM |
| Rabbit immunized with CFA | 0.165 | 0.214 | 0.168 | 0.189 | 0.183 | 0.219 | 0.158 | 0.198 |
| | 0.172 | 0.206 | 0.153 | 0.197 | 0.191 | 0.211 | 0.167 | 0.211 |
| Rabbit immunized with Candida in CFA | 1.631 | 1.548 | 0.218 | 0.334 | 1.328 | 1.265 | 1.325 | 1.189 |
| | 1.752 | 1.397 | 0.227 | 0.326 | 1.397 | 1.217 | 1.314 | 1.198 |
| Human serum A | 1.358 | 1.135 | 0.187 | 0.279 | 1.122 | 0.931 | 1.124 | 0.986 |
| | 1.416 | 1.284 | 0.192 | 0.268 | 1.032 | 0.897 | 1.097 | 0.915 |
| Human serum B | 2.167 | 1.762 | 0.254 | 0.341 | 1.811 | 1.456 | 1.728 | 1.289 |
| | 2.258 | 1.695 | 0.232 | 0.326 | 1.692 | 1.394 | 1.677 | 1.316 |
| Human serum C | 0.826 | 1.236 | 0.185 | 0.245 | 0.679 | 1.032 | 0.658 | 0.987 |
| | 0.784 | 1.148 | 0.192 | 0.238 | 0.656 | 0.969 | 0.612 | 1.035 |

When food antigens were incubated with three different rabbit anti-Candida sera and three different human anti-Candida sera, ELISA optical densities were reduced between 15 and 40% (Table 3). Significant absorption of Candida antibody occurred with baker's yeast, brewer's yeast, soy, wheat and beef. No absorption occurred with orange.

TABLE 3

| | IgG Anti-Candida Antibody Levels | | | | | | | |
|---|---|---|---|---|---|---|---|---|
| | Before | After Absorption with | | | | | | |
| Antibody Source | Ab-sorption | Bakers Yeast | Brewers Yeast | Soy | Wheat | Milk | Orange | Beef | Adrenal |
| RABBIT A | 1.65 | 1.01 | 1.28 | 1.34 | 1.38 | 1.41 | 1.67 | 1.24 | 1.33 |
| RABBIT B | 2.45 | 1.64 | 1.92 | 2.18 | 2.19 | 2.23 | 2.48 | 1.97 | 2.15 |
| RABBIT C | 1.26 | 0.87 | 0.99 | 1.05 | 1.11 | 1.15 | 1.25 | 1.08 | 1.06 |
| HUMAN A | 1.85 | 1.25 | 1.45 | 1.59 | 1.63 | 1.64 | 1.83 | 1.51 | 1.59 |
| HUMAN B | 1.28 | 0.71 | 0.98 | 1.14 | 1.11 | 1.02 | 1.30 | 1.12 | 1.03 |
| HUMAN C | 0.86 | 0.52 | 0.65 | 0.69 | 0.72 | 0.67 | 0.87 | 0.58 | 0.64 |

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of detecting immunological cross reactivity between a plurality of tissue antigens and *Candida albicans* or *Candida tropicalis* antigens in an individual infected with *Candida albicans* or *Candida tropicalis*, comprising the steps of:

isolating serum from said individual;

contacting said tissue antigens with said serum; and determining whether said serum binds one or more of said tissue antigens.

2. The method of claim 1, wherein said contacting and determining steps comprise enzyme linked immunosorbent assay or immunodiffusion.

3. The method of claim 1, further comprising separating said tissue antigens by gel electrophoresis and transferring said antigens to a membrane prior to said contacting step.

4. The method of claim 1, wherein one or more of said tissue antigens has a molecular weight of about 36 kDa or 72 kDa.

5. A method of detecting immunological cross reactivity between food antigen and *Candida albicans* or *Candida tropicalis* antigens in an individual infected with *Candida albicans* or *Candida tropicalis*, comprising the steps of:

isolating serum from said individual;

contacting said food antigens with said serum; and determining whether said serum binds one or more of said food antigens.

6. The method of claim 5, wherein said contacting and determining steps comprise enzyme linked immunosorbent assay or immunodiffusion.

7. The method of claim 5, further comprising separating said tissue antigens by gel electrophoresis and transferring said antigens to a membrane prior to said contacting step.

8. The method of claim 7, wherein said food antigens have molecular weights between 1 kDa and 250 kDa.

9. The method of claim 8, wherein said food antigens have molecular weights between about 10 kDa and about 90 kDa.

10. A method of determining a diet plan for a patient having a *Candida albicans* or *Candida tropicalis* infection, comprising:

isolating serum from said patient;

contacting a plurality of food antigens with said serum; and determining whether said serum binds one or more of said food antigens, wherein said food antigens which bind said serum are avoided.

11. The method of claim 10, wherein said contacting and determining steps comprise enzyme linked immunosorbent assay or immunodiffusion.

12. The method of claim 10, further comprising separating said tissue antigens by gel electrophoresis and transferring said antigens to a membrane prior to said contacting step.

13. The method of claim 12, wherein said food antigens have molecular weights between 1 kDa and 250 kDa.

14. The method of claim 13, wherein said food antigens have molecular weights between about 10 kDa and about 90 kDa.

* * * * *